(12) United States Patent
Stoller et al.

(10) Patent No.: US 8,932,987 B2
(45) Date of Patent: Jan. 13, 2015

(54) COMPOSITION AND METHOD FOR STRESS MITIGATION IN PLANTS

(75) Inventors: Jerry Stoller, Houston, TX (US); Albert Liptay, Houston, TX (US); Ronald Salzman, College Station, TX (US)

(73) Assignee: Stoller Enterprises, Inc., Houston, TX (US)

(*) Notice: Subject to any disclaimer, the term of this patent is extended or adjusted under 35 U.S.C. 154(b) by 66 days.

(21) Appl. No.: 13/433,050

(22) Filed: Mar. 28, 2012

(65) Prior Publication Data

US 2012/0295788 A1    Nov. 22, 2012

Related U.S. Application Data

(63) Continuation-in-part of application No. 13/429,014, filed on Mar. 23, 2012, now abandoned.

(60) Provisional application No. 61/469,044, filed on Mar. 29, 2011.

(51) Int. Cl.
*A01N 59/00* (2006.01)
*A01N 43/90* (2006.01)
*A01N 47/36* (2006.01)
*C05F 11/10* (2006.01)

(52) U.S. Cl.
CPC .............. *A01N 43/90* (2013.01); *A01N 47/36* (2013.01); *C05F 11/10* (2013.01)
USPC ........................................................ 504/124

(58) Field of Classification Search
USPC ........................................................ 504/124
See application file for complete search history.

(56) References Cited

U.S. PATENT DOCUMENTS

| | | | | |
|---|---|---|---|---|
| 4,581,056 A | * | 4/1986 | Nooden et al. | 71/28 |
| 2005/0197253 A1 | * | 9/2005 | Stoller et al. | 504/138 |

FOREIGN PATENT DOCUMENTS

| WO | 2000019821 A1 | 4/2000 |
|---|---|---|
| WO | 0172130 A1 | 10/2001 |
| WO | 2007028165 A2 | 3/2007 |
| WO | 2009067190 A1 | 5/2009 |
| WO | 2011038389 A1 | 3/2011 |

OTHER PUBLICATIONS

Veerasamy et al. "Leaf Senescence and Protein Metabolism in Creeping Bentgrass Exposed to Heat Stress and Treated with Cytokinins," J. Amer. Soc. Hort. Sci. 132(4):467-472; 2007.*

(Continued)

*Primary Examiner* — Susan McCormick Ewoldt
(74) *Attorney, Agent, or Firm* — Gary L. Bush; Andrews Kurth LLP

(57) ABSTRACT

A composition and method to mitigate plant autophagy and/or apoptosis of newly developing cells in plants grown under environmentally stressful growing conditions, such as high temperature. Exogenous application of a cytokinin, preferably kinetin, to either the roots or the foliage (i.e., flowers and leaves) of plants has been discovered to overcome, or at least substantially mitigate, autophagy when applied during or just prior to flowering. Experimental results indicate that high temperature-induced autophagy, and subsequent new cell apoptosis, is the result of a deficiency of cytokinin in the plant tissues. The application of low concentrations of potassium together with the cytokinin appears to provide a synergistic effect by amplifying the effect of the cytokinin to lessen autophagy and increase crop productivity.

4 Claims, 2 Drawing Sheets

(56) References Cited

OTHER PUBLICATIONS

Stoyanova et al. "Influence of drought, high temperature, and carbamide cytokinin 4-PU-30 on photosynthetic activity of plants. 2. Chloroplast ultrastructure of primary bean leaves," Photosynthetica 37 (4):621-625, 1999.*

Veerasamy et al. "Leaf Senescence and Protein Metabolism in Creeping Bentgrass Exposed to Heat Stress and Treated with Cytokinins," J. Amer. Soc. Hort. Sci. 132(4):467-472 (2007).*

Liptay, A., Vandierendonck, P., Liptay, A. M. J. Novel trichomes increase stamen stiffness in mung bean flowers, Canadian Journal of Plant Science, Dec. 10, 1993, Agriculture Canada, pp. 335-337, Research Station, Ontario, Canada.

Cheikh, Nordine, Jones, Robert J. Disruption of Maize Kernel Growth and Development by Heat Stress, Plant Physiol. (1994) 106: pp. 45-51, University of Minnesota, St. Paul, Minnesota.

Szekeres, Mikloss, et al. Brassinosteroids Rescue the Deficiency of CYP90, a Cytochrome P450, Controlling Cell Elongation and De-etiolation in *Arabidopsis*, Cell. Apr. 19, 1996, pp. 171-182, vol. 85, Cell Press.

Lolle, Susan J.; Hsu, Wendy; Pruitt, Robert E. Genetic Analysis of Organ Fusion in *Arabidopsis thaliana*, Genetics, Mar. 3, 1998, pp. 607-619, 149, Harvard University, Cambridge, Massachusetts.

Takahashi, Naoki, et al. The DNA replication checkpoint aids survival of plants deficient in the novel replisome factor ETG1, The EMBO Journal, May 7, 2008, pp. 1840-1851, vol. 27, No. 13, European Molecular Biology Organization, Ghent University, Gent, Belgium.

Csizinszky, A., et al. Foliar and Soil-Applied Biostimulant Studies with Microirrigated Pepper and Tomato, Proc. Fla. State Hort. Soc. (1990), pp. 113-117, 103, Gulf Coast Research and Education Center, University of Florida, Bradenton, Florida.

Becker Underwood, Salute WSP—Turfgrass Conditioner with Potassium Silicate (WSP is registered trademark of Becker Underwood) Ames, Iowa.

International Search Report and Written Opinion of Counterpart application PCT/US12/30981, dated Jun. 28, 2012.

Translation of Opposition to Costa Rican (counterpart) Application No. 2013-558, dated Mar. 18, 2014.

* cited by examiner

COMPOSITION AND METHOD FOR STRESS MITIGATION IN PLANTS

CROSS-REFERENCE TO RELATED APPLICATIONS

This application is a continuation-in-part of U.S. patent application Ser. No. 13/429,014, filed Mar. 23, 2012, which itself claims priority to U.S. Provisional Application Ser. No. 61/469,044, filed Mar. 29, 2011.

BACKGROUND OF THE INVENTION

1. Field of the Invention

This invention relates generally to a method and composition for mitigating plant autophagy or the degradation of older plant cells to supply nutrients to deficient newly-forming plant cells, which can occur during development (e.g., flowering) of new plant cells under stressful conditions, such as high temperatures. Moreover, this invention relates to the enhanced development of seeds, and consequently, the increased yield of harvestable grains from plants, including crop plants, that experience environmentally stressful growing conditions during development and growth.

2. Description of the Related Art

Traditionally, mineral fertilizers have been predominately applied to growing crop plants. Difficulties arise, however, when external stresses impede successful plant development, especially of grain or seed crops and/or other crops. Physical stresses, such as those inflicted by environmental temperatures being either too low or too high, and in particular high temperatures, are especially problematic. Moreover, the state-of-the-art agronomic practice does not employ plant growth regulators to overcome a plant's difficulty, due to such stresses, in producing sufficient amounts of nutrients, e.g., sugars, to prevent autophagy (i.e., cannibalization of previously-formed plant cells by newly-forming cells to compensate for a dearth of cell nutrients). It is well known that mineral fertilizers provide sixteen minerals that are necessary for crop growth and development. Signaling molecules, such as plant growth regulators or other molecules, are known to enhance crop productivity through the expression of certain genes. Furthelore, much research has been conducted into the use of plant growth regulators and their effects on plant growth and development. However, until disclosure of the invention herein, it has not been known that the application of certain "signaling molecules" improves plant productivity by mitigating plant autophagy caused by environmental stresses, such as high growing temperatures.

Considering the sheer amount of research into techniques and compositions to improve food production as well as the continual need for greater food production to feed an exponential human population growth, there is a long felt and unfulfilled need for improved methods and compositions to improve plant productivities, especially in view of higher environmental temperatures and other harsher growing conditions.

3. Identification of Objects of the Invention

An object of the invention is to accomplish one or more of the following:

Provide a method and composition to enhance the productivity and growth of crop plants;

Provide a method and composition to enhance the productivity and growth of crop plants grown under harsh environmental stresses;

Provide a method and composition to enhance the productivity and growth of plants grown under high temperature conditions;

Provide a method and composition to increase the synthesis of nutrients by plants;

Provide a method and composition to mitigate plant autophagy and/or apoptosis;

Provide a method and composition to enhance productivity and crop growth during the vegetative stages of crop growth, prior to the reproductive stages of crop growth;

Provide a method and composition to enhance the seed size of grain crops, and therefore crop yield, under high temperature stress by increasing the availability of water for grain sizing; and Provide a method and composition to enhance the seed size of grain crops and therefore crop yield under high temperature stress by increasing the availability of water for grain sizing.

Other objects, features, and advantages of the invention will be apparent from the following specification and drawings to one skilled in the art.

SUMMARY OF THE INVENTION

The objects identified above, along with other features and advantages of the invention are incorporated into a method and composition for growing plants, especially crop plants, to be more productive and/or resilient to stressful growing conditions, such as high temperature. When growing temperatures are too high, the development of flowers and subsequent embryos (seeds) is known to be compromised, with the concomitant result that productivity of crop grains or other types of agronomic harvest is impaired and crop yields can be drastically decreased. Under extreme growing conditions, such as high temperatures, plants experience an inability to produce the nutrients, such as sugars, necessary for conducting normal anabolic processes (i.e., flower and embryo/seed development). To compensate for this dearth of nutrients, plants growing under these stress conditions typically undergo autophagy, or self-cannibalization, to secure the necessary nutrients to the newly formed cells.

Exogenous application to the plant canopy (i.e. leaves and flowers) of the plant growth regulator/hormone cytokinin has been discovered to prevent such autophagy by inducing the necessary production of sufficient nutrients (i.e., sugars) for the growth of new plant cells (i.e., successful and complete seed development). It is thought that genes controlling for increased levels of photosynthates (i.e., plant sugar/energy producers) are triggered by exogenous application of cytokinin. Additionally, the application of low concentrations of potassium along with the cytokinin has been found to substantially increase the effect of the cytokinin. Such results are unexpected with such low potassium concentrations, because they differ from the physiological effects normally attributed to higher application rates of fertilizer-grade potassium. It is thought that the application of low concentrations of potassium act much like other signaling molecules (e.g., hormones) in stimulating transcription of particular genes, such as the genes that express cytokinin effects, or provide an enhanced level of energy or enhance other hormones that have an effect on increasing yields such as abscisic acid or responsiveness to same. The synergy from the application of low concentrations of potassium and cytokinin to growing plants may also be realized under lower stress growing conditions.

The disclosed composition and its method of application represents a practical approach to mitigating plant autophagy, and any ensuing apoptosis, that results from stressful plant growing conditions, such as high temperatures. The method preferably includes the application of a plant hormone, primarily a cytokinin, to the foliage and/or flowers of plants at or about the time of the beginning of plant flowering (e.g., during meiosis and when pollen is about to enter dehiscence). This autophagy-inhibiting agent is preferably the cytokinin, kinetin, however, other forms of cytokinin may be used singularly or in combination, such as zeatin, various forms of zeatin, N6-benzyl adenine, N6-(delta-2-isopentyl) adenine, 1,3-diphenyl urea, thidiazuron, CPPU (forchlorfenuron) or other chemical formulations with cytokinin-like activity. Preferably, but optionally, a low concentration of potassium is also applied together with the plant hormone to enhance the effects of the plant hormone as previously described.

In a first step, the cytokinin plant hormone is readied for application to the plants to be treated. The cytokinin plant hormone is preferably applied to the plants as an aqueous solution. Therefore, readying the cytokinin plant hormone may include one or more of the following activities: diluting the cytokinin plant hormone in sufficient water to create the desired concentration of cytokinin in the applied mixture/composition, adding low concentrations of potassium to the cytokinin plant hormone mixture/composition to enhance the effects of the applied cytokinin, loading the cytokinin plant hormone with or without potassium (or an aqueous mixture thereof) into a sprayer or tank for subsequent application to the plants to be treated, calibrating the sprayer or dosing applicator to meter the desired amount of the cytokinin plant hormone mixture to the plants to be treated and transporting the cytokinin plant hormone with or without potassium (or an aqueous mixture thereof) to the location of the plants to be treated.

Preferably, the cytokinin concentration in an undiluted aqueous solution ranges from about 0.01% to about 0.10%. A commercially-available, undiluted cytokinin solution, X-Cyte (a product of Stoller USA, Houston, Tex.), supplies the preferred cytokinin concentration of about 0.04%. At the preferred cytokinin concentration, the undiluted aqueous solution of cytokinin is applied in a second step to plants to be treated at the rate of between about ¼ to 4 pints solution per acre of growing plants and more preferably between 1 to 2 pints solution per acre of growing plants. Such application equates to a rate of between about 0.09 to about 0.76 grams cytokinin per acre of growing plants (diluted in 60 gallons of water per acre), and more preferably, at a rate of between about 0.19 to about 0.38 grams cytokinin per acre of growing plants (diluted in 60 gallons of water per acre). Potassium, if applied with the cytokinin, is preferably applied at very low concentrations. The potassium application rates are preferably between about ¼ lb. to about 2 lbs. per acre, more preferably between about ½ lb. to about 1½ lbs. per acre, and most preferably about 1 lb. per acre. The cytokinin and/or potassium can be applied either to the leaves, as stated above, or to the soil at the same concentrations. It may be applied to the soil in any appropriate fashion, such as, for example, in an opened furrow near the plant roots, which furrow may subsequently be closed. It may also be applied with various forms of irrigation, such as overhead or drip tape, or furrow irrigation, among others.

BRIEF DESCRIPTION OF THE DRAWINGS

By way of illustration and not limitation, the invention is described in detail hereinafter on the basis of the accompanying figures, in which.

DESCRIPTION OF THE PREFERRED IMPLEMENTATIONS OF THE INVENTION

Figure 1:
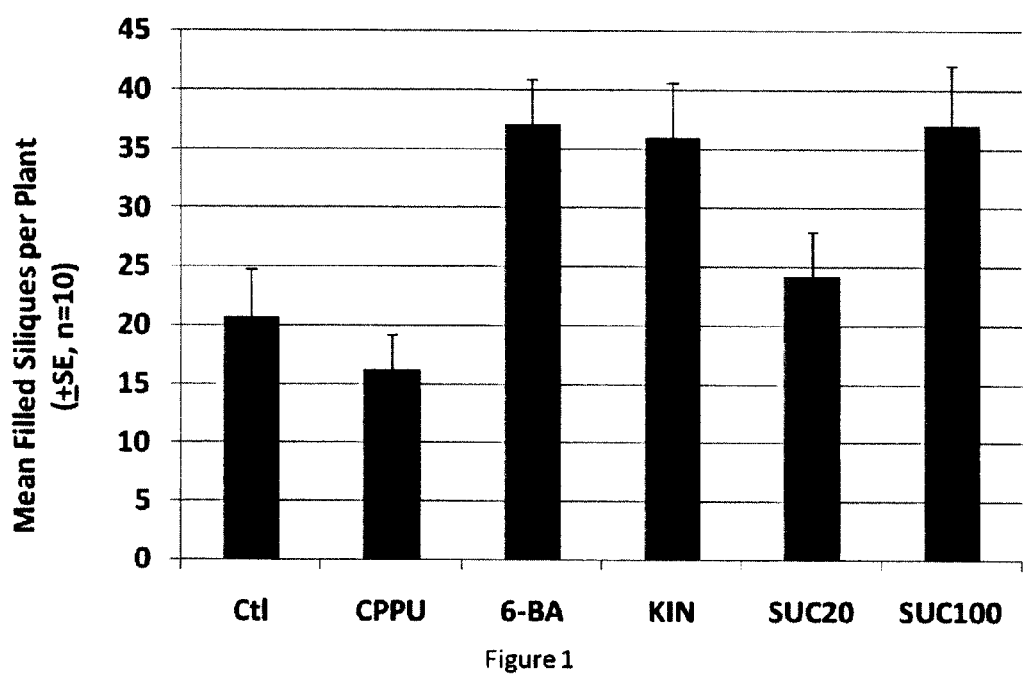
FIG. 1 is a histogram of experimental results testing whether impaired seed/silique development under high temperature growth conditions is caused by a nutrient/sugar insufficiency, which may incite apoptosis of newly-forming plant cells via autophagy.
Figure 2:
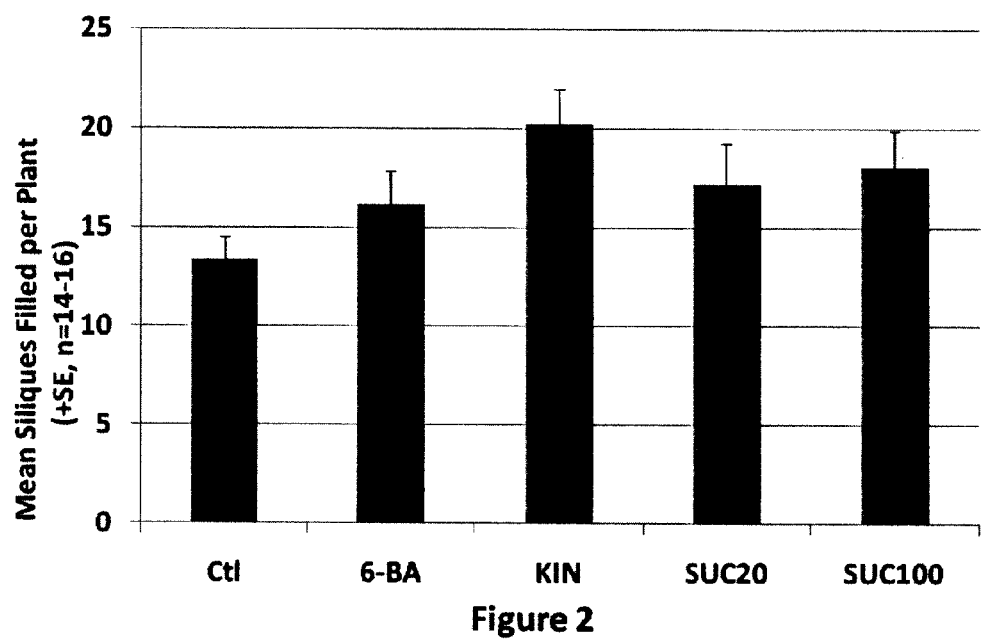
FIG. 2 is a histogram of experimental data that verifies the results obtained in FIG. 1, namely that high temperature yield reduction, caused by autophagy, is mainly due to an insufficiency of the plant growth regulator/hormone, cytokinin.

A preferred implementation of the invention addresses one or more of the deficiencies of the prior art and incorporates at least one of the objects previously identified. The invention employs a plant growth regulator, preferably a cytokinin, which when appropriately applied to plants has been discovered to enhance the synthesis and transfer of sufficient nutrients, such as sugars, for the growth and development of the reproductive parts (e.g., in particular, the pollen) of plants grown under stressful conditions, such as high temperatures. For the purposes of this invention, high growing temperatures include growing temperatures above about 25 degrees Celsius (77 degrees Fahrenheit), but more commonly growing temperatures above about 30 degrees Celsius (86 degrees Fahrenheit). Even a temperature greater than about 20 degrees Celsius (68 degrees Fahrenheit) may be considered a "high" temperature, depending on the plant type (e.g., wheat barley and rye) and/or locality (e.g., distance from the earth's poles). Such high temperatures have been found to compromise crop plant productivity. This is thought to be the result of the reduction of cytokinin plant hormones in the plant due to the high temperatures.

A reduction in the level of cytokinin in the plant tissues incites autophagy—self-cannibalization—of healthy plant tissues to provide the required nutrients for reproductive development. The stress of autophagy can compromise seed formation (Cheikh et al. 1994), structural strength and/or physical integrity of the reproductive organs (and thus successful egg fertilization) (Liptay et al. 1994), cell arrangement and organ functionality (Lolle et al. 1998), cell replication (Takahshi et al. 2008) and cell growth (Szekeres et al. 1996). These stress effects are due to autophagy of pre-formed tissues in the various processes of plant growth and development mentioned previously. Furthermore, this autophagy results in apoptosis of potential crop products, thereby significantly reducing crop yield.

Exogenous applications of cytokinin to the flowers and leaves (i.e., foliage) of plants provides the spatially-required, growth regulator signaling effect needed for enhanced synthesis of nutrients/sugars for use by tender new cells. The cytokinin and/or potassium can also be applied to the soil in which plants are growing at the same concentrations. It may be applied to the soil in any appropriate fashion, such as, for example, in an opened furrow near the plant roots, which furrow may subsequently be closed. It may also be applied with various forms of irrigation, such as overhead or drip tape, or furrow irrigation, among others. Enhancement of nutrient synthesis, via cytokinin application, is believed to result in a more complete development of the biological tissues for plant reproduction. Specifically, the availability of an adequate supply of nutrients/energy leads to the successful development of the male sperm, including the various tissues and biological signals responsible for its development. An adequate energy source also aids in the various stages of development of the pollen in which the sperm are protected by encasement. Also, adequate nutrients/energy are available to assist the male sperm in its journey from the pollen grain, through the developing pollen tube and into the female ovary for fertilization of the egg. Thus, cytokinin application results in the successful formation of seed embryos and associated tissues of the crop plant, thereby overcoming autophagy and any resultant apoptosis.

Additionally, the application of low concentrations of potassium along with the cytokinin has been found to substantially increase the effect of the cytokinin on plant tissues. Such results are unexpected and differ from the physiological effects normally attributed to higher application rates of typical fertilizer-grade potassium. The physiological effects of higher applied potassium concentrations include: maintaining turgidity in the plants and thus ensuring a water supply, neutralizing anions helping to stabilize pH of the cytoplasm, and general metabolic processes. To induce these physiological effects, the concentration of applied potassium must be on the order of typical fertilizers. The low concentrations of potassium, disclosed herein, employed for signaling effect are at least ten percent lower than typical potassium fertilizer applications, such as those described in U.S. Pat. No. 4,581,056 issued to Nooden et al. or in A. A. Csizinszky, *Foliar and Soil-Applied Biostimulant Studies with Microirrigated Pepper and Tomato*, 103 PROC. FLA. STATE HORT. SOC. 113-17 (1990). It is thought that potassium, applied in low concentrations, acts much like other signaling molecules (e.g., hormones) in aiding transcription of particular genes, such as the genes that are expressed in response to applied cytokinin. Potassium, if applied with the cytokinin, is preferably applied at very low concentrations between about ¼ lb. to about 2 lbs. per acre, more preferably between about ½ lb. to about 1½ lbs. per acre, and most preferably about 1 lb. per acre. The signaling effect of the potassium has been found to be increasingly diminished for potassium application rates greater than about 2 lbs. per acre.

A preferred implementation of the invention facilitates the successful synthesis of nutrients/sugars, such that these nutrients/sugars (i.e., chemical energy) may be transferred to the developing male plant organs. The method preferably includes the application of a plant hormone, primarily a cytokinin, to the foliage and/or flowers of plants at or about the time of plant flowering. The period of potential effectiveness of cytokinin application may range from several weeks prior to flower emergence, up to and including flower emergence, pollination, and during subsequent embryo development. A preferred time is during the process of meiosis, when pollen mother cells my fail to differentiate, or fail to divide. This time of meiosis occurs in dicot plants during an interval after flower bud differentiation, but before the flowers open. In monocot plants, such as grains, it corresponds approximately to the "early boot" stage (Feekes stage 10.0) in grain development. Another preferred time is during pollen release from the tapetum and pollen sacs, when pollen is about to enter dehiscence (or shed). In dicot plants, this generally falls within the period ranging from immediately before the opening of the flower up until the flower dies and falls off the plant. In monocot plants, pollen release corresponds approximately to Feekes stage (10.5.1) in grain development. The application of cytokinin after flowering may also enhance the development of the embryo under high temperature growing conditions and thereby increase yield.

The autophagy-inhibiting agent is preferably the cytokinin, kinetin, however, other forms of cytokinin may be used singularly or in combination, such as zeatin, various forms of zeatin, N6-benzyl adenine, N6-(delta-2-isopentyl) adenine, 1,3-diphenyl urea, thidiazuron, CPPU (forchlorfenuron) or other chemical formulations with cytokinin-like activity. Preferably, but optionally, a low concentration of potassium is also applied together with the plant hormones to enhance the effects of the plant hormone, cytokinin.

In a first step, the cytokinin plant hormone is readied for application to the plants to be treated. The cytokinin plant hormone is preferably applied to the plants as an aqueous solution. Application of agricultural chemicals may be accomplished in any of several ways well known to those skilled in the art, including but not limited to, spraying, drip lines, side dressing, etc. Therefore, readying the cytokinin plant hormone may include one or more of the following activities: diluting the cytokinin plant hormone in sufficient water to create the desired concentration of cytokinin in the applied mixture/composition, adding a low concentration of potassium to the cytokinin plant hormone mixture/composition to enhance the effect of the applied cytokinin, loading the cytokinin plant hormone with or with out potassium (or an aqueous mixture thereof) into a sprayer or tank for subsequent application to the plants to be treated, calibrating the sprayer or dosing applicator to meter the desired amount of the cytokinin plant hormone to the plants to be treated and transporting the cytokinin plant hormone with or without potassium (or an aqueous mixture thereof) to the location of the plants to be treated.

Preferably, the cytokinin concentration in an undiluted aqueous solution ranges from about 0.01% to about 0.10%. A commercially-available, undiluted cytokinin product, X-Cyte (a product of Stoller USA, Houston, Tex.), supplies the preferred cytokinin concentration of about 0.04%. At the preferred cytokinin concentration, the undiluted aqueous solution of cytokinin is applied in a second step to plants to be treated at the rate of between about ¼ to 4 pints solution per acre of growing plants and more preferably between 1 to 2 pints solution per acre of growing plants. Such application equates to a rate of between about 0.09 grams to about 0.76 grams of cytokinin per acre of growing plants (diluted in 60 gallons of water per acre for a sprayed/applied solution), and more preferably, at a rate of between about 0.19 to about 0.38 grams cytokinin per acre of growing plants (diluted in 60 gallons of water per acre for a sprayed/applied solution), depending on the specific plant/crop species. Thus, as disclosed above, the amount of cytokinin applied to the growing plants (1 to 2 pints of undiluted cytokinin solution per acre, which is equivalent to 0.1 ppm to 1.66 ppm cytokinin of the sprayed/applied solution per acre) is much lower than previous cytokinin applications to growing plants. In fact, the preferred application rates are more than ten fold lower than other reported ranges of cytokinin application, which are from about 20 ppm to about 400 ppm as suggested by N. G. Denny, *User Guide of Plant Growth Regulators*. If the duration of flower development is lengthy, the application may need to be repeated for the newly developing flowers.

The cytokinin and/or potassium (discussed in further detail below) can be applied either to the leaves of the plants, or to the soil at the same concentrations. It may be applied to the soil in any appropriate fashion, such as, for example, in an opened furrow near the plant roots, which furrow may subsequently be closed. It may also be applied with various forms of irrigation, such as overhead or drip tape, or furrow irrigation, among others.

Potassium, if applied together with the cytokinin, is also preferably applied at low concentrations. (Alternatively, the potassium may be applied prior to or after a separate application of cytokinin. However, such separate applications are not optimal, because they are more energy and time intensive.) The potassium is preferably applied as a potassium salt, such as that found in potash, however other forms of potassium known to those skilled in the art may be equally employed. The potassium application rates are preferably between about ¼ lb. to about 2 lbs. per acre (equivalent to about 500 ppm to about 4,000 ppm potassium of the sprayed solution per acre), more preferably between about ½ lb. to about 1½ lbs. per acre, and most preferably about 1 lb. per acre. The synergistic effects of applying low concentrations of cytokinin along with low concentrations of potassium to growing plants may not be limited to high stress growing conditions but may also be realized under lower stress growing conditions.

Preferred implementations of the invention are further described in the following several examples. However, these examples are not meant in any way, and should not be interpreted, to limit the scope of the invention disclosed herein.

EXAMPLE 1

Experiments were conducted to determine the extent to which the plant growth regulator, cytokinin, when appropriately applied to plants growing in high temperature environments, enhanced sugar levels and increased the transfer of sugars to energy deficient portions of the plant. These experiments were also designed to determine whether the plant tissues under high temperature stress suffered from one or both of two potential problems: First, whether under high temperature stress, there is a deficiency of cytokinin in the plant tissue. Second, whether under high temperature stress, there is degradation of the cytokinin (which is a normal process to regulate the balance of plant growth regulators in plant tissues, in this case by reducing the amount of active cytokinin in the plant tissue).

The data from these experiments, as shown in FIGS. 1 and 2, clearly indicate that the problem suffered by plants subjected to high temperature stresses during their flowering phase is an inadequacy of cytokinin in the reproductive tissues of the plants. The results further show that appropriate, exogenous cytokinin application, as disclosed herein, increases plant development and crop yields in high temperature growing environments (i.e., increases the number and quality of seeds that are properly developed, thus increasing yield at harvest). FIG. 1 is a histogram of experimental results testing whether impaired seed/silique development under high temperature growth conditions is caused by a nutrient/sugar insufficiency, which may incite apoptosis of newly-forming plant cells by autophagy and FIG. 2 is a histogram of experimental data that verifies the results obtained in FIG. 1, namely that high temperature yield reduction, caused by autophagy, is mainly due to an insufficiency of the plant growth regulator/hormone, cytokinin.

These experiments employed the model crop plant, *Arabidopsis thaliana*, whose genome was mapped as early as the year 2000. To ensure uniformity, the tested plants were selected such that they were in the beginning stages of flowering and had balanced numbers of flowers across groups. The control agent as well as all tested agents were applied in a water solution containing 0.01% Silwet® super spreader (obtained from General Electric) to the leaves and flowers (i.e., foliage) of the tested plants. As shown in FIG. 1, a control agent (Ctl) consisting of an aqueous solution of 0.01% Silwet® super spreader was applied to a control plant group. A second tested agent consisting of N-(2-chloro-pyridin-4-yl)-N-phenyl-urea (CPPU) at 100 μg/l (0.1 ppm) was applied to a second plant grouping to test whether the difficulty in seed formation is due to cytokinin insufficiency or overactive enzymes that break down cytokinin in the plant. The third and fourth agents tested consisted of 6-benzyl adenine (6-BA) and kinetin (KIN)—both cytokinins—each applied at the rate of 100 μg/l (0.1 ppm). Finally, the fifth and sixth agents tested consisted of sucrose sugars applied in solutions of 20 mM (SUC 20) and 100 mM (SUC100), respectively, applied as readily-available energy sources.

Aqueous solutions of the tested agents prepared to the stated concentrations/doses were sprayed onto test groups of flowers and leaves (i.e., foliage) of *Arabidopsis thaliana* until runoff at one day prior to heat exposure and again at four days after the beginning of heat exposure. The total duration of heat exposure was fourteen (14) days. The growing temperatures were maintained at between 33-36 degrees Celsius during sixteen (16) hour days, and at about 25 degrees Celsius during eight (8) hour nights. The experiments were conducted on poly(methyl methacrylate)-enclosed shelves, i.e., Plexiglass®-enclosed shelves, using four dual fluorescent lamps and a thermostat-controlled exhaust fan. The seed pods (i.e. siliques), filled with developed seeds (siliques >7 mm long and/or >1 mm wide and/or bearing seeds), were counted just prior to the beginning of the experiment, and again after fourteen (14) days of heat exposure treatments.

As shown in FIG. 1, the plant growth regulator, cytokinin, can mitigate the sugar deficiency in the plant tissues caused by high growing temperatures, thus preventing autophagy. This result is indicated by the increased number of seeds (i.e., siliques) in the cytokinin tested agents—6-benzyl adenine (6-BA) and kinetin (KIN). The slightly negative results encountered with the N-(2-chloro-pyridin-4-yl)-N-phenyl-urea (CPPU) tested agent (i.e., a cytokinin oxidase inhibitor) combined with the positive results encountered with the cytokinin tested agents clearly indicate that the problem of high temperature induced autophagy is due to a cytokinin insufficiency (i.e., lack of energy synthesis for the newly foiling cells). It should be noted that the two sucrose tested agents also alleviated the sugar/photosynthate deficiency thereby preventing plant autophagy. However, sucrose testing agents provide expensive, temporary relief, because the sucrose breaks down rapidly in situ.

FIG. 2 presents an additional set of experimental results that reinforce the results obtained for the previous experiment (FIG. 1). The second experiment was conducted in the same manner and using the same control and tested agent concentrations as the first experiment, with the exception of CPPU application. Thus, the respective aqueous solutions as used in the first experiment, with the exception of CPPU, were sprayed onto test groups of *Arabidopsis thaliana* foliage until runoff at one day prior to heat exposure and again at four days after the beginning of heat exposure. The total duration of heat exposure was fourteen (14) days. The growing temperatures were maintained at between 33-36 degrees Celsius during sixteen (16) hour days, and at about 25 degrees Celsius during eight (8) hour nights. The experiments were conducted on poly(methyl methacrylate)-enclosed shelves, i.e., Plexiglass®-enclosed shelves, using four dual fluorescent lamps and a thermostat-controlled exhaust fan. The seed pods (i.e. siliques), filled with developed seeds (siliques >7 mm long and/or >1 mm wide and/or bearing seeds), were counted just prior to the beginning of the experiment, and again after fourteen (14) days of heat exposure treatments. The results of the second experiment may be similarly interpreted as the results of the first experiment, thereby confirming that the plant growth regulator, cytokinin, can mitigate the sugar deficiency in the plant tissues caused by high growing temperatures, thus reducing autophagy.

EXAMPLE 2

In this example, the effect of the plant growth regulator cytokinin, specifically kinetin, applied at the beginning of flowering and two to four weeks thereafter to field-grown beans (i.e., lima beans) in Gustine, Calif. was observed. Growing temperatures up to approximately 35 degrees Celsius were recorded. Table 2 (below) provides the results of this replicated, randomized experiment. The lima bean yields were increased significantly (i.e., less seeds succumbed to autophagy and seed death or collapse) when the aqueous solution of kinetin was applied just prior to flowering to the lima bean foliage at either a rate of one pint per acre or two pints per acre. The difference of "t" test of 5% is significant.

TABLE 1

Crop Yield for Kinetin Solution Application at Flowering for Rates of 0 pt/acre, ½ pt/acre, 1 pt/acre and 2 pt/acre
Lima Bean Yield
Gustine, CA
Year 2010

| Average | Average Yield (lb/plot) | Average Yield (lb/plot) | Average Yield (lb/plot) | Average Yield (lb/plot) |
|---|---|---|---|---|
| X-Cyte pt/acre | 0 | 0.5 | 1 | 2 |
| Average yield (lb/plot) | 6.86 | 6.915 | 7.845 | 8.11375 |
| t test vs. control |  | 0.416532 | 0.000115 | 0.000307 |
| t test vs. ½ pt/acre |  |  | 0.003132 | 0.006917 |
| t test vs. 1 pt/acre |  |  |  | 0.09629 |
| rep 1 | 7.13 | 6.47 | 8.13 | 8.61 |
| rep 2 | 6.84 | 8.34 | 8.02 | 8.02 |
| rep 3 | 6.59 | 7.11 | 7.65 | 7.83 |
| rep 4 | 6.8 | 6.68 | 8.07 | 8.37 |
| rep 5 | 7.17 | 6.45 | 7.38 | 8.51 |
| rep 6 | 7 | 7.17 | 7.55 | 6.85 |
| rep 7 | 6.7 | 6.49 | 7.91 | 8.53 |
| rep 8 | 6.65 | 6.61 | 8.05 | 8.19 |

EXAMPLE 3

In this example, the effect of the plant growth regulator/hormone, cytokinin, applied together with low concentrations of potassium, was observed. The cytokinin that was field-applied was X-Cyte, as previously disclosed. In these unreplicated field trials, conducted in Ohio over a three year period, potassium at ½ lb. to 1 lb. per acre and cytokinin at 1 pint per acre were applied to field corn. The average increase in yield attained by applying potassium, in addition to cytokinin, was approximately fifteen (15) bushels per acre.

EXAMPLE 4

In this example, the effect of the plant growth regulator cytokinin, specifically kinetin, and applied at various times before the reproductive stages of growth, was observed. In Table 2, V7, V10, V13, and V16 refer to stages of growth of the corn plant. V7 refers to the growth stage where the collar of the seventh leaf is visible, V10 refers to the growth stage where the collar of the tenth leaf is visible, V13 refers to the growth stage where the collar of the thirteenth leaf is visible, and V16 refers to the growth stage where the collar of the sixteenth leaf is visible. V16 is also just prior to the reproductive stage of growth. The corn crops were grown in Weslaco, Tex. The water levels were either none (i.e., simply rain referred to as dryland), or drip through a "drip tape" (i.e., drip irrigation whereby sufficient water was applied for more optimal growth of the crop). Results are given for yield (measured in bushels per acre), and the weight of the seed (measured in grams per 1,000 kernels). T tests indicate whether there were differences. All treatments with exogenous cytokinin (in this case kinetin) enhanced yield in a highly significant fashion. Seed size was generally increased about the same with more optimal watering both for the untreated control and the exogenously applied cytokinin. However, under dryland conditions (no added water or irrigation) the cytokinin treatment increased seed size in a highly significant fashion over the untreated control.

TABLE 2

Treatment of field-grown corn crops before the reproductive stage of growth with cytokinin, in this case kinetin, on the effect of the treatment on crop yield (measured in bushels of grain per acre), and seed size (measured in grams per 1,000 kernels of seed).

| EXPT | Stage | Variety | Water | Sowing Harvest Dates | Yield Bu/acre | SD Yield | Yield T test vs con P= | 1,000 Kernel wt g | SD Kernel wt | Kernel wt T test vs con P= |
|---|---|---|---|---|---|---|---|---|---|---|
| 1 | control | B25DC25 R80 | Drip | Oct. 1, 2011 Jan. 7, 2012 | 174 | 11.6 |  | 296 | 7.1 |  |
| 1 | V10 | " | " | Oct. 1, 2011 Jan. 7, 2012 | 259 | 7.0 | 0.01% | 298 | 2.2 | NS |
| 1 | V16 | " | " | Oct. 1, 2011 Jan. 7, 2012 | 311 | 8.8 | 0.01% | 298 | 1.0 | NS |
| 2 | control | Asgrow 7573 | Dry land | Mar. 15, 2011 Jul. 15, 2011 | 91 | 7.4 |  | 227 | 5.1 | — |
| 2 | V10 | " | " | Mar. 15, 2011 Jul. 15, 2011 | 149 | 3.3 | 0.01% | 244 | 5.0 | 0.01% |
| 3 | control | H2684162 | Dry land | Feb. 15, 2011 Jun. 10, 2011 | 101 | 2.2 |  | 260 | 15.1 | — |
| 3 | V16 | " | " | Feb. 15, 2011 Jun. 10, 2011 | 207 | 4.9 | 0.015 | 296 | 3.6 | 0.01% |
| 3 | V13 | " | " | Feb. 15, 2011 Jun. 10, 2011 | 208 | 9.1 | 0.01% | 299 | 10.1 | 0.01% |
| 3 | V10 | " | " | Feb. 15, 2011 Jun. 10, 2011 | 211 | 4.6 | 0.01% | 296 | 6.6 | 0.01% |
| 3 | V7 | " | " | Feb. 15, 2011 Jun. 10, 2011 | 212 | 6.4 | 0.01% | 295 | 9.6 | 0.015 |

The Abstract of the disclosure is written solely for providing the United States Patent and Trademark Office and the public at large with a means by which to determine quickly from a cursory inspection the nature and gist of the technical disclosure, and it represents one preferred implementation and is not indicative of the nature of the invention as a whole.

While some implementations of the invention have been illustrated in detail, the invention is not limited to the implementations shown; modifications and adaptations of the disclosed implementations may occur to those skilled in the art. Such modifications and adaptations are in the spirit and scope of the invention as set forth in the claims hereinafter:

What is claimed is:

1. A method of mitigating plant autophagy in plants grown under a high stress environmental condition, said method comprising the steps of:
   readying a plant hormone for application to plants, said plant hormone being primarily cytokinin,
   applying said plant hormone in an aqueous solution to said plants during or just prior to flowering, said aqueous solution having a concentration of between about 0.01 wt % to about 0.1 wt % cytokinin, said aqueous solution applied to said plants at a rate of about ¼ pint to about 4 pints per acre, and
   applying potassium to the foliage or flowers after flowering of said plants or to the soil in which the plants are growing at the rate of between 0.25 and 0.50 lbs. per acre.

2. The method of claim 1 wherein,
   said high stress environmental condition is a daytime temperature of greater than about 30 degrees Celsius.

3. The method of claim 2 wherein,
   said daytime temperature of greater than 30 degrees Celsius occurs during or just prior to flowering.

4. A method for mitigating plant autophagy resulting from high temperature, comprising the steps of,
   preparing a cytokinin solution of between about 0.01% wt to about 0.10% wt % in water,
   applying said cytokinin solution at a rate of about ¼ pint to about 4 pints per acre to plants when daytime temperature is greater than about 30 degrees Celsius and when said plants are beginning to flower or during plant flowering, and
   applying potassium to the foliage or flowers after flowering of said plants or to the soil in which the plants are growing at the rate of between 0.25 and 0.50 lbs. per acre.

* * * * *